(12) United States Patent  (10) Patent No.: US 9,417,224 B1
 Shah  (45) Date of Patent: Aug. 16, 2016

(54) MOBILE APPLICATION FOR GARDENING

(71) Applicant: Alex Shah, San Diego, CA (US)

(72) Inventor: Alex Shah, San Diego, CA (US)

( * ) Notice: Subject to any disclaimer, the term of this patent is extended or adjusted under 35 U.S.C. 154(b) by 0 days.

(21) Appl. No.: 14/335,922

(22) Filed: Jul. 20, 2014

Related U.S. Application Data

(60) Provisional application No. 61/858,111, filed on Jul. 24, 2013.

(51) Int. Cl.
 *G01N 33/00* (2006.01)
(52) U.S. Cl.
 CPC ................... *G01N 33/0098* (2013.01)
(58) Field of Classification Search
 None
 See application file for complete search history.

(56) References Cited

U.S. PATENT DOCUMENTS

2011/0091112 A1\* 4/2011 Engtrom et al. ............. 382/197

OTHER PUBLICATIONS

Data Validation, Wikipedia: the free encyclopedia, Apr. 18, 2012, http://en.wikipedia.org/w/index.php?title=Data_validation &oldid=487998925.\*
Al-Hiary, H., et al. "Fast and accurate detection and classification of plant diseases." Machine learning 14 (2011): 5.\*

\* cited by examiner

*Primary Examiner* — Stephen R Koziol
*Assistant Examiner* — Raphael Schwartz
(74) *Attorney, Agent, or Firm* — Clause Eight IPS; Michael Catania

(57) ABSTRACT

A system and method using a native mobile application for gardening is disclosed herein. An image of a plant or plant disease is uploaded and sent to a site for identification and advise from an expert or expert database. A response is provided to the gardener, along with helpful information.

1 Claim, 17 Drawing Sheets

MOBILE APPLICATION FOR GARDENING

CROSS REFERENCE TO RELATED APPLICATION

The Present Application claims priority to U.S. Provisional Patent Application No. 61/858,111, filed on Jul. 24, 2013, which is hereby incorporated by reference in its entirety.

STATEMENT REGARDING FEDERALLY SPONSORED RESEARCH OR DEVELOPMENT

Not Applicable

BACKGROUND OF THE INVENTION

1. Field of the Invention

The present invention generally relates to mobile applications related to gardening.

2. Description of the Prior Art

The prior art discusses gardening.

General definitions for terms utilized in the pertinent art are set forth below.

APP is a software application for a mobile phone such as a smart phone.

Application Programming Interface (API) is a collection of computer software code, usually a set of class definitions, that can perform a set of related complex tasks, but has a limited set of controls that may be manipulated by other software-code entities. The set of controls is deliberately limited for the sake of clarity and ease of use, so that programmers do not have to work with the detail contained within the given API itself.

BLUETOOTH technology is a standard short range radio link that operates in the unlicensed 2.4 gigaHertz band.

Code Division Multiple Access ("CDMA") is a spread spectrum communication system used in second generation and third generation cellular networks, and is described in U.S. Pat. No. 4,901,307.

CRM (Customer Relationship Management) is a widely-implemented strategy for managing a company's interactions with customers, clients and sales prospects. CRM involves using technology to organize, automate, and synchronize business processes and the like—principally sales activities, but also business processes and the like for marketing, customer service and technical support.

Direct Inward Dialing ("DID") involves a carrier providing one or more trunk lines to a customer for connection to the customer's private branch exchange ("PBX") and a range of telephone lines are allocated to this line.

FTP or File Transfer Protocol is a protocol for moving files over the Internet from one computer to another.

GSM, Global System for Mobile Communications is a second generation digital cellular network.

Hypertext Transfer Protocol ("HTTP") is a set of conventions for controlling the transfer of information via the Internet from a web server computer to a client computer, and also from a client computer to a web server, and Hypertext Transfer Protocol Secure ("HTTPS") is a communications protocol for secure communication via a network from a web server computer to a client computer, and also from a client computer to a web server by at a minimum verifying the authenticity of a web site.

Internet is the worldwide, decentralized totality of server computers and data-transmission paths which can supply information to a connected and browser-equipped client computer, and can receive and forward information entered from the client computer.

Media Access Control (MAC) Address is a unique identifier assigned to the network interface by the manufacturer.

Organizationally Unique Identifier (OUI) is a 24-bit number that uniquely identifies a vendor, manufacturer, or organization on a worldwide basis. The OUI is used to help distinguish both physical devices and software, such as a network protocol, that belong to one entity from those that belong to another.

Probe Request: A frame that contains the advertisement IE for a device that is seeking to establish a connection with a proximate device.

Probe Response: A frame that contains the advertisement IE for a device. The Probe Response is sent in response to a Probe Request.

SSID (Service Set Identifier) is a 1 to 32 byte string that uniquely names a wireless local area network.

Transfer Control Protocol/Internet Protocol ("TCP/IP") is a protocol for moving files over the Internet.

URL or Uniform Resource Locator is an address on the World Wide Web.

User Interface or UI is the junction between a user and a computer program. An interface is a set of commands or menus through which a user communicates with a program. A command driven interface is one in which the user enter commands. A menu-driven interface is one in which the user selects command choices from various menus displayed on the screen.

Web-Browser is a complex software program, resident in a client computer, that is capable of loading and displaying text and images and exhibiting behaviors as encoded in HTML (HyperText Markup Language) from the Internet, and also from the client computer's memory. Major browsers include MICROSOFT INTERNET EXPLORER, NETSCAPE, APPLE SAFARI, MOZILLA FIREFOX, and OPERA.

Web-Server is a computer able to simultaneously manage many Internet information-exchange processes at the same time. Normally, server computers are more powerful than client computers, and are administratively and/or geographically centralized. An interactive-form information-collection process generally is controlled from a server computer, to which the sponsor of the process has access.

Wireless Application Protocol ("WAP") is an open, global specification that empowers users with mobile wireless communication devices (such as mobile phones) to easily access data and to interact with Websites over the Internet through such mobile wireless communication device. WAP works with most wireless communication networks such as CDPD, CDMA, GSM, PDC, PHS, TDMA, FLEX, reflex, iDEN, TETRA, DECT, DataTAC, Mobitex and GRPS. WAP can be built on most operating systems including PalmOS, WINDOWS, CE, FLEXOS, OS/9, JavaOS and others.

WAP Push is defined as an encoded WAP content message delivered (pushed) to a mobile communication device which includes a link to a WAP address.

Wireless AP (access point) is a node on the wireless local area network (WLAN) that allows wireless devices to connect to a wired network using Wi-Fi, or related standards.

There is a need for providing gardeners with a rapid response to an inquiry which is correct and beneficial to the gardener.

SUMMARY OF THE INVENTION

A method and system for using a mobile application to identify unknown plants or plant diseases. An image of a plant or plant disease is uploaded and sent to a site for identification and advise from an expert.

One aspect of the present invention is a method for using a mobile native application resident on a mobile communication device to identify an unknown plant or a plant disease. The method includes receiving an image inquiry message at a server from a mobile native application of a mobile communication device. The mobile communication device comprises a camera component and a GPS component. The image message comprises an image, geographical location information for the image, and comments about the image provided by an end user. The image is of a plant, plant disease or plant pest. An inquiry concerns the identification of the plant, plant disease or plant pest. The method also includes analyzing the image at the server to determine if the image is acceptable. The method also includes transferring the image at the server for substantive content analysis. The method also includes categorizing the image into a predetermined category. The method also includes preparing a response to identify the plant, plant disease or plant pest. The response is based on the image, the geographical location, the comments and information contained in a database of the server. The method also includes transmitting a response message from the server to the mobile native application of a mobile communication device. The response message identifies the plant, plant disease or plant pest.

Another aspect of the present invention is a system for using a mobile application resident on a mobile communication device to identify an unknown plant or a plant disease. The system includes a server, a network and a mobile communication device. The mobile communication device comprises a mobile native application, a camera component and a GPS component. The camera component of the mobile communication device is configured to take an image of a plant, plant disease or plant pest. The GPS component is configured to generate a geographical location of the image. The mobile native application is configured to generate an image inquiry message comprising the image, the geographical location information for the image, and comments about the image provided by an end user. An inquiry concerns the identification of the plant, plant disease or plant pest. The server is configured to analyze the image to determine if the image is acceptable. The server is configured to transfer the image for substantive content analysis. The server is configured to categorize the image into a predetermined category. The server is configured to prepare a response to identify the plant, plant disease or plant pest, wherein the response is based on the image, the geographical location, the comments and information contained in a database of the server. The server is configured to transmit a response message from the server to the mobile native application of a mobile communication device, wherein the response message identifies the plant, plant disease or plant pest.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
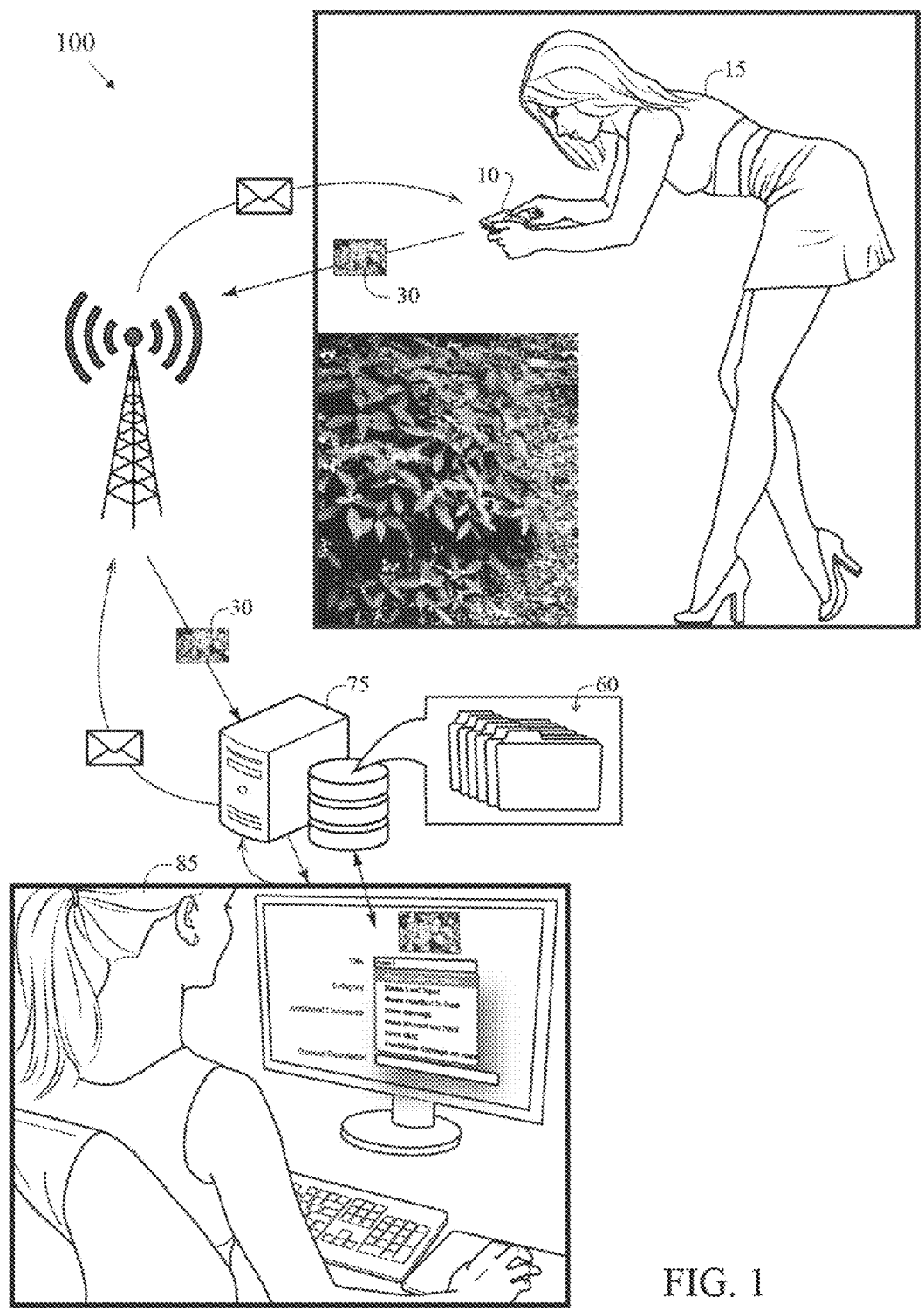
FIG. 1 is an illustration of a system of the present invention.

As shown in FIG. 1, a system for using a mobile application resident on a mobile communication device to identify an unknown plant or a plant disease is generally designated 100. A gardener (end-user) 15 takes an image 30 of a plant with her mobile communication device 10. She then sends a message with the image 30 over a communications network to a server 75 that is in communication with a database 60. At the server site 75, a non-expert 85 receives the message with the image 30 and processes the message with the image 30 for further analysis as set forth below. The analysis includes identification and further advice for the gardener.

FIGS. 2-7 illustrate displays of a native mobile application resident on the mobile communication device 10.

The client side experience is set forth below. The client device is preferably a mobile communication device 10 such as a mobile phone or a tablet computer. The mobile communication device 10 has a native mobile application resident in a memory of the mobile communication device 10. The native application is preferably downloaded from the APP STORE provide by Apple Computer, or the ANDROID application website. Alternatively, the client device is a laptop computer or a desktop computer, and the application is a web application.

Mobile applications for smartphones are currently available for iOS and ANDROID operating systems.

In practice, end-users (owners of the client device) upload a photo plus optional geolocation using the mobile application 20. The geolocation assist in identifying the plant or disease, and assist in determining what advice to provide to the end-user gardener.

Figures 2, 3:
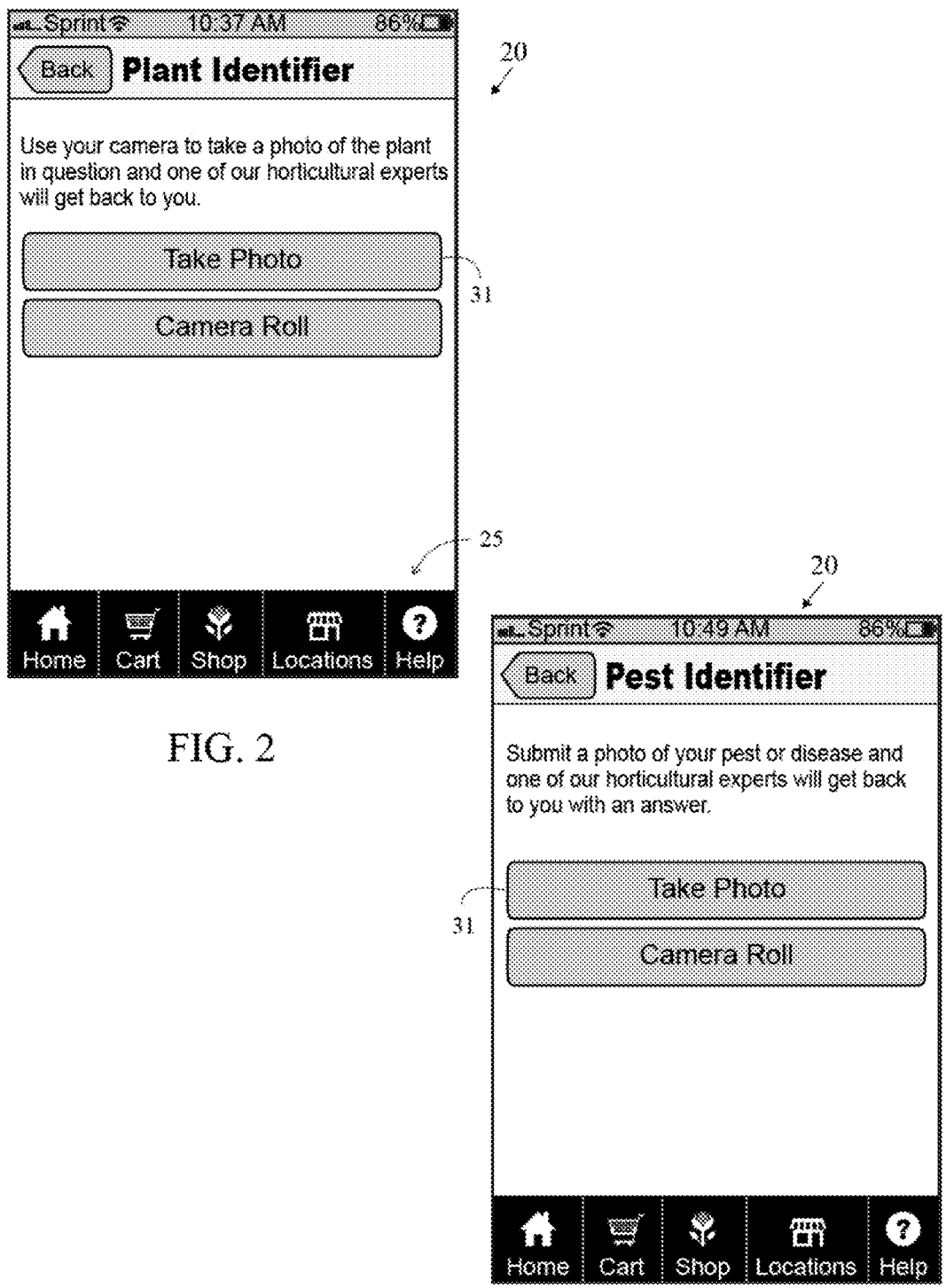
FIG. 2 is a display page of a mobile application.
FIG. 3 is a display page of a mobile application.

First, as shown in FIG. 2, the end user 15 opens the application 20 on the mobile communication device 10 and accesses a plant identifier page. The plant identifier page preferably provides two options: take a new image or use an existing image from a camera roll in a memory of the mobile communication device 10. An application menu 25 is also provided on each page for allowing the user to make immediate actions. The end user 15 uses the take photo button 31 to take a new image.

Alternatively, as shown in FIG. 3, the end user 15 opens the application 20 and accesses a pest identifier page for identifying a pest or a disease. The pest identifier page preferably provides two options: take a new image or use an existing image from a camera roll in a memory of the mobile communication device 10. An application menu 25 is also provided on each page for allowing the user to make immediate actions. The end user 15 uses the take photo button 31 to take a new image of a pest.

Figure 4:
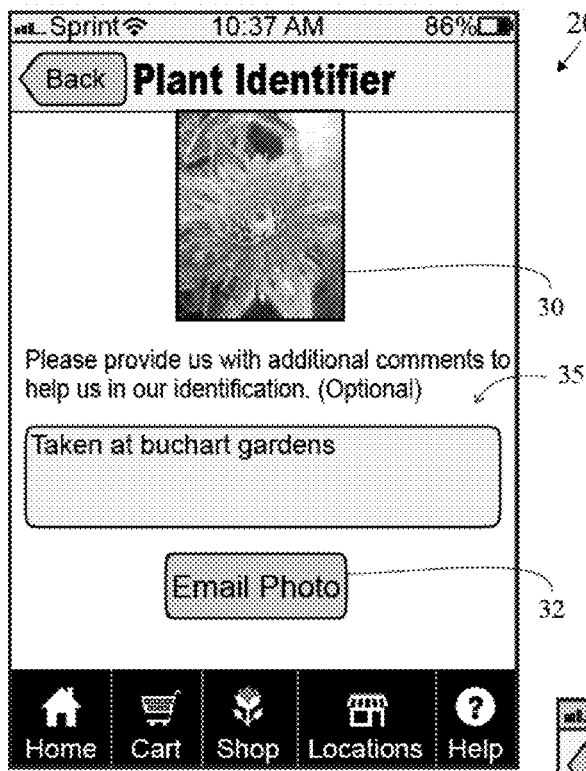
FIG. 4 is a display page of a mobile application.
Figure 5:
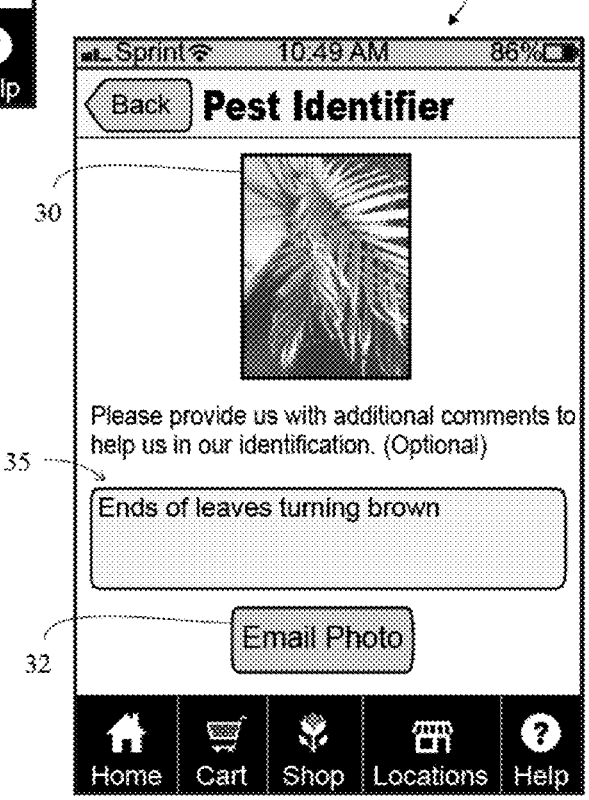
FIG. 5 is a display page of a mobile application.

Once the image 30 is attached to the page, then (optionally), as shown in FIGS. 4 and 5, the end-user 15 adds any additional comments that may help in the identification of the plant or disease in the comment menu 35. A transmission button 32 is provided for sending the message to the server 75 over a network, such as the Internet or a communications network.

Figure 6:
FIG. 6 is a display page of a mobile application.
Figure 7:
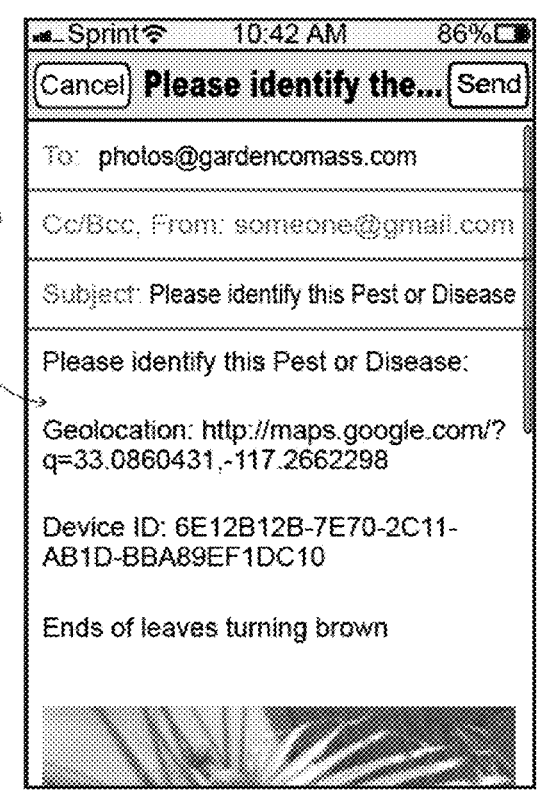
FIG. 7 is a display page of a mobile application.

As shown in FIGS. 6 and 7, the image message is then submitted to the server side 75. In a preferred current application, the image message submission 40 is sent over HTTP (possibly HTTPS, i.e. HTTP with SSL security layer), as shown in FIGS. 5 and 6. In an alternative embodiment, the submission 40 is sent as an Email. As shown, a geo-location (latitude and longitude) is included in the message transmission which provides location information to the server-side 75.

Once received, the message is preferably processed by a team of horticultural experts. The response is preferably delivered by Email. Alternatively, the response is delivered as a "smartphone" notification, i.e. iOS or Android notification.

Figure 8:
FIG. 8 is a display page of a response.

The first message 45 received by the end-user from the server-side 75 (iGarden) is to inform the end user that the image message has been received, as shown in FIG. 8.

The message 45 also contains queue position 46 information, which informs the end-user of their position in the queue. This provides the end-user an idea of how long the end user 15 has to wait before they receive a response from the experts on the server-side 75. In the event that the response takes more than 24 hours, a 2nd message is sent to let the end-user know that the experts of the server-side 75 are still working on their request. The 2nd message shows their new position in the queue.

From within the application, the end-user sees a list of all their photo submissions, answers, and where the end user is in the queue for any unanswered questions.

Figure 9:
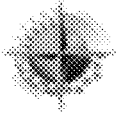
FIG. 9 is a display page of an answer.

Once an answer has been found, a response message 50 is sent to the end user. The response message 50 has the following attributes, as shown in FIG. 9.

The response message 50 includes recommendations 51 for other flowers that the end-user may be interested in. For diseases and pests inquiries, the response message 50 recommends products that will help the diseased plant. In addition, the response message 50 includes a rating link 52 to allow the end-user to rate the native application on the iOS or Android stores.

Figure 10:
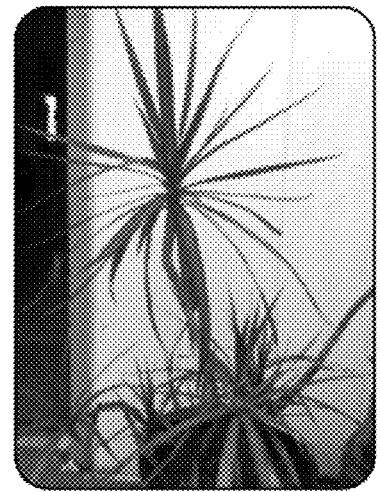
FIG. 10 is a display page of another type of answer.
Figure 10A:
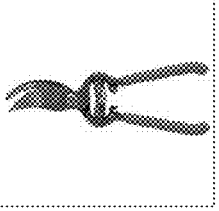
FIG. 10A is a webpage of an answer link from FIG. 10.

In an alternative embodiment shown in FIG. 10, the response message 50 contains a link 53 to link to a web site. As shown in FIG. 10A, the answer and product recommendation web page of the web site 55 is tailored for the end-user's question. The page is constructed so that the page is viewed from any mobile or desktop client device (or from within the mobile application itself).

The link 53 of the response message 50 links the mobile device 10 to the web site, so that pertinent information about the end-user, such as their email, home address, credit card, etc. is linked to their custom answer so an end-user can quickly make a purchase. In other words, an end-user only has to provide their personal information to the server side 75 once and an account is created for the end user based on their email and unique phone identifier (telephone number, MAC address, UUID). The web page also contains a login 56 button for the end user to access their account.

An account is also created for the end-user from their email. The end user is able to set up a password for their account.

FIGS. 11-15 illustrate the server side 75 backend processing.

Figure 11:
FIG. 11 is a display page of the GUI of the backend for processing submissions.

Once an image 30 is received on the server-side 75, the image 30 is stored on the server side 75 in a database 60 and is placed into the "submitted by user" folder 61, as shown in FIG. 11.

Figure 12:
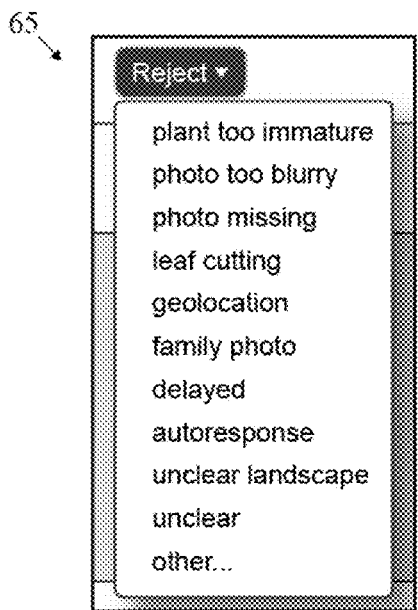
FIG. 12 is a display page of the GUI of the backend for rejecting submissions.

Preferably then a non-horticultural expert decides which folder to drop the image question into, based on the type of image (e.g. flower, tree, vegetable, fruit, house plant, weed, lawn, pest, disease) and geolocation. The non-expert moves the image from the "submitted by user" to the "ready for review by . . . " folder. In addition to moving the photos, the non-expert rejects any incoming image that does not meet minimum criteria: i.e. geolocation information, photo invalid, blurry photo, photo taken too far away, photo taken too close, etc, according to a menu 65, as shown in FIG. 12.

If the non-expert makes a mistake in their assignment of the image (photo) to an expert, the expert can reassign it to another expert or put it back into the general box.

Figure 13:
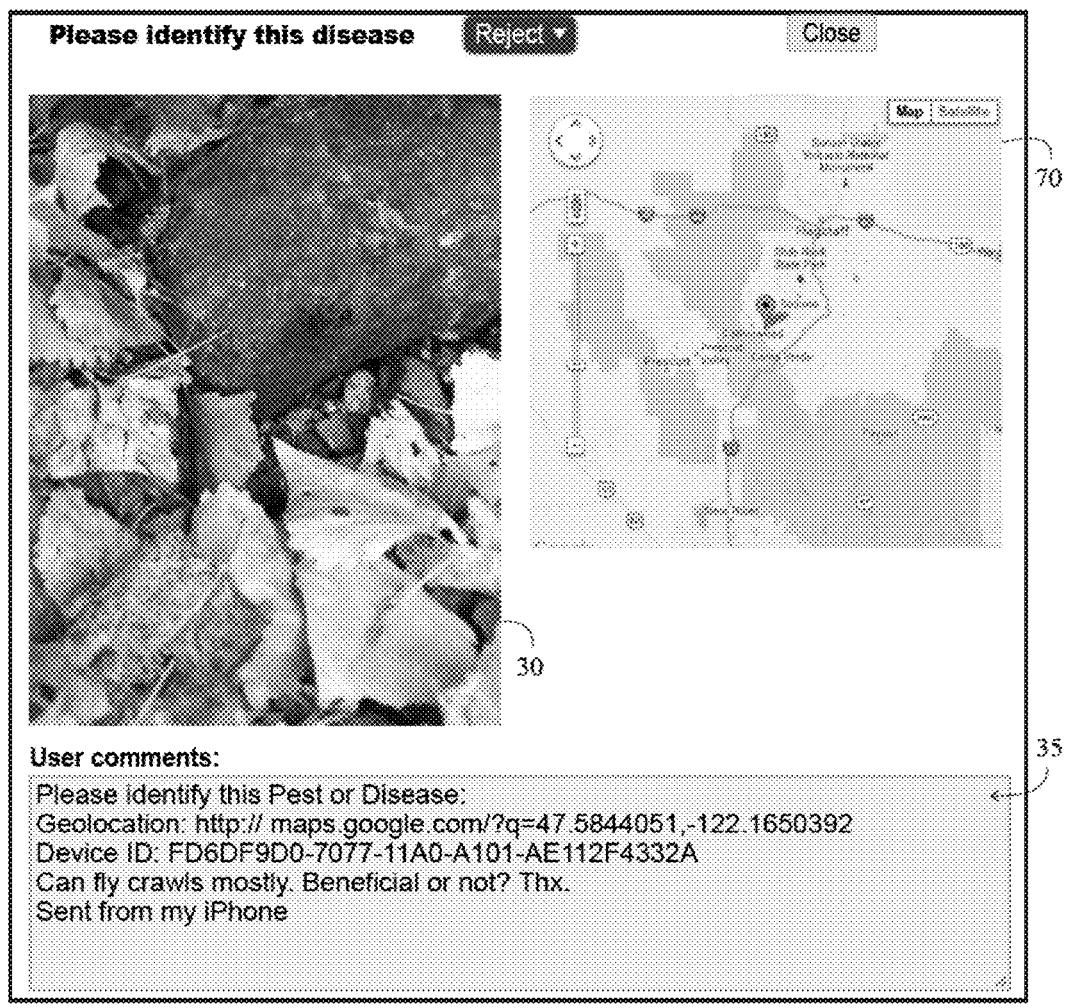
FIG. 13 is a display page of an answer for rejecting a submission.

The expert sees the image 30, geolocation 70, and user comments 35, as shown in FIG. 13.

Figure 14:
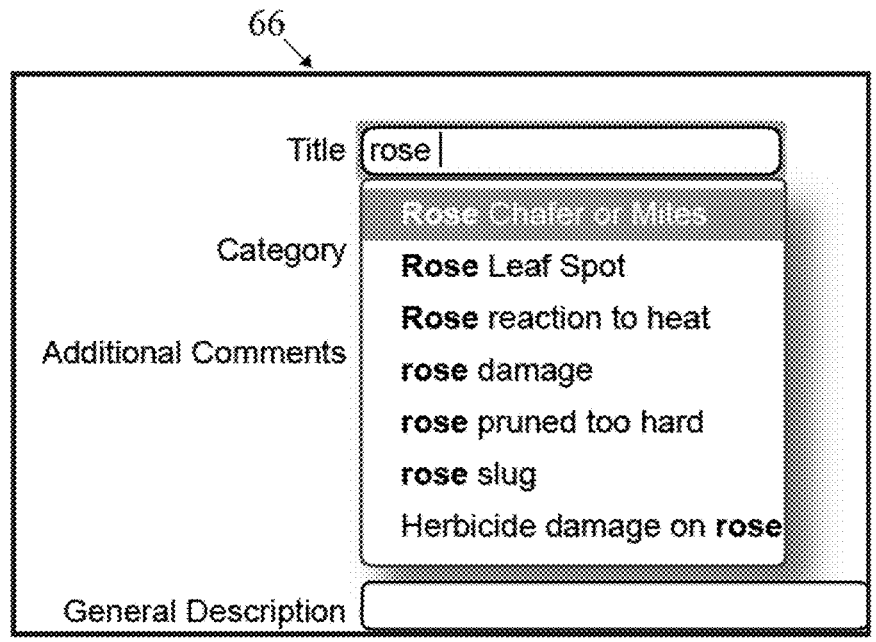
FIG. 14 is a drop down menu page for a title of the GUI.

When answering the image question, a title 66 must give given, as shown in FIG. 14.

As words are typed, the system automatically suggests answers that have been given in the past. If a good match is found, then the expert can select it and avoid having to type in the full answer from scratch.

Figure 15:
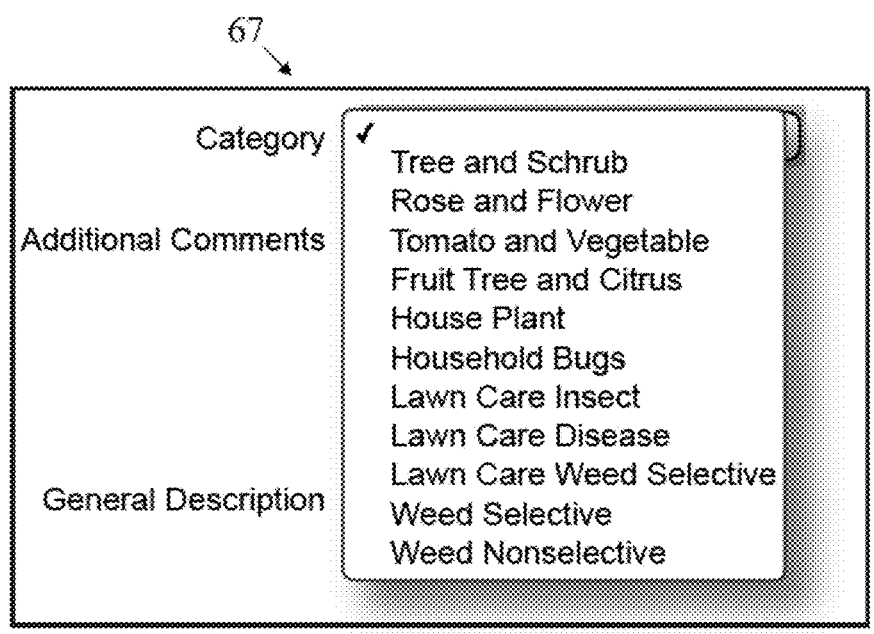
FIG. 15 is a drop down menu page for a category of the GUI.

The expert also picks a category 67 for the answer, as shown in FIG. 15.

The category is used to automatically suggest relevant products/solutions for the given photo submission, along with the expert's answer.

Design Center

Figure 16:
FIG. 16 is a display page of a mobile application.

In addition to human experts answering questions, the system of the server-side 75 searches for plant suggestions from a submitted mobile camera photo, as shown in FIG. 16.

Figure 17:
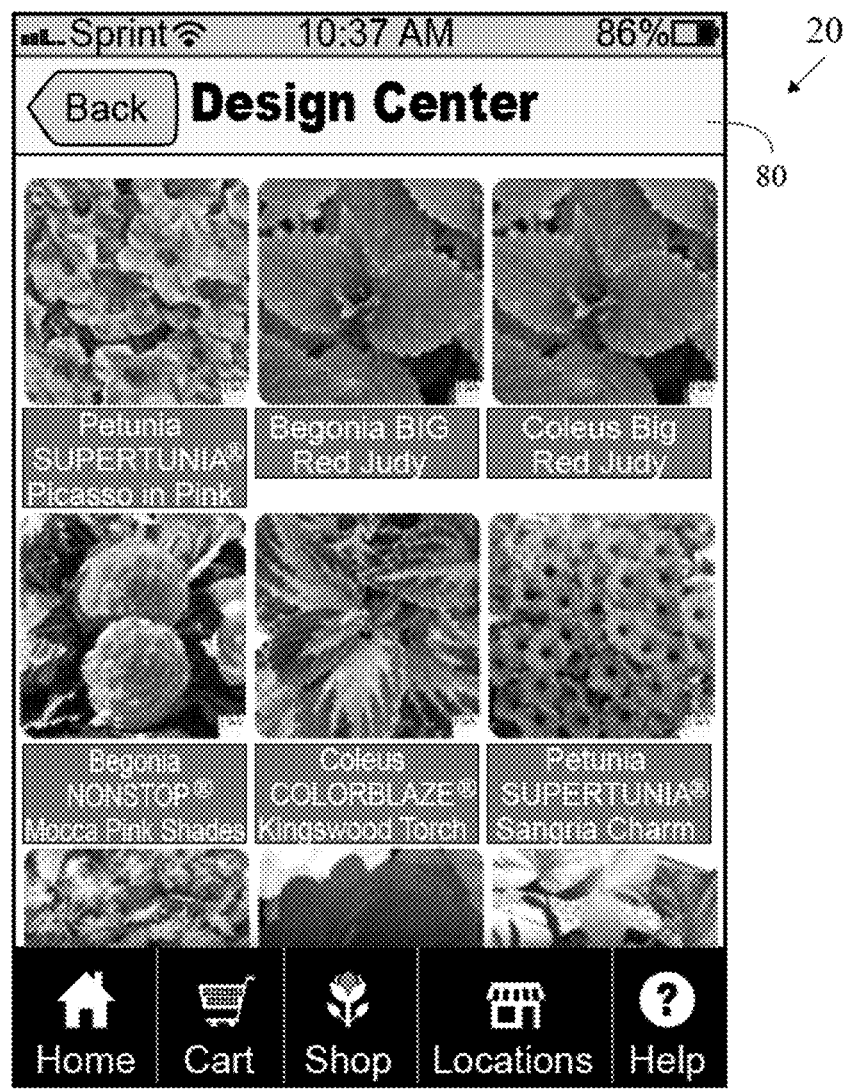
FIG. 17 is a display page of a mobile application.

The uploaded photo is analyzed and a color and texture feature vector is created. This feature vector is then compared to a database of available plants. Close matches are stored and sent down to the end-user's mobile device, as shown in FIG. 17.

Once the end-user clicks on a plant, he can purchase it. Specifically, one or more items can be added to a cart and then purchased together.

Figure 18:
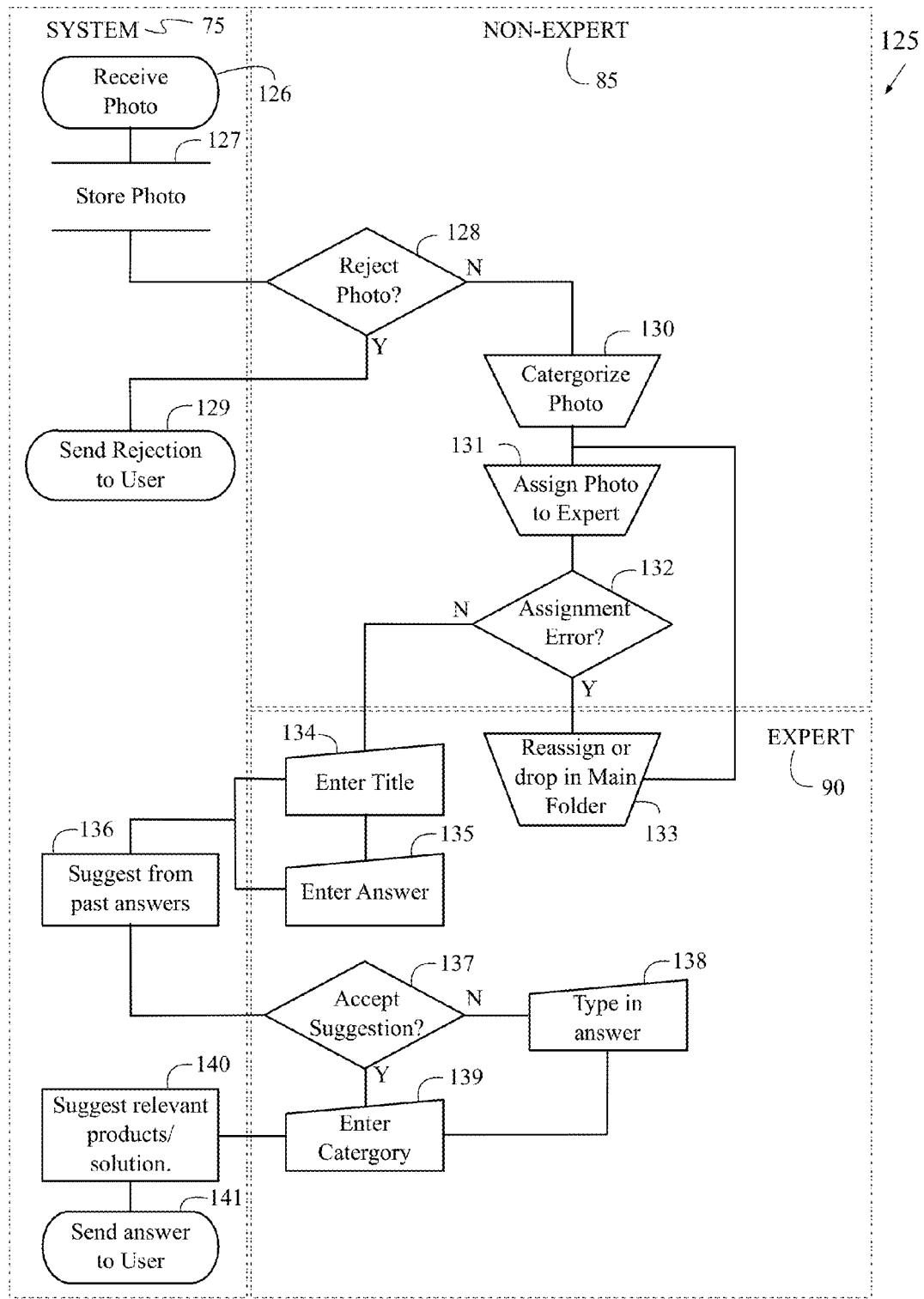
FIG. 18 is a flow chart of the present invention.

FIG. 18 illustrates a flow chart of a method 125 for identifying an image of a plant submitted from a mobile application of a mobile device 10 to a server-side 75. At step 126, a photo 30 is received at the server 75. At step 127, the photo 30 is stored in the database server database 60. The photo is then analyzed by a non-expert technician 85, or a computer program to determine if the image is acceptable. At decision 128, the non-expert 85 (or computer program) either rejects or accepts the photo. If the photo is rejected, it is sent to the end user at block 129. If the photo 30 is accepted, then at step 130 the photo 30 is categorized. At step 131, an expert 90 is assigned to analyze the photo. At decision block 132, it is determined if there is an assignment error. If yes, then at block 133 the photo 30 is reassigned. If no, then at block 134 a title is entered for the photo 30. At block 135 an answer is provided to the question, what plant is this? At block 136, past answers are also suggested to the expert 90. At decision 137, the suggestion is either accepted or rejected. If rejected, then at block 138 an answered is typed into the response. If the suggestions are accepted, then at block 139 a category is entered and at block 140 products and solutions are also provided for the response. At block 141, the response is sent to the end-user.

Figure 20:
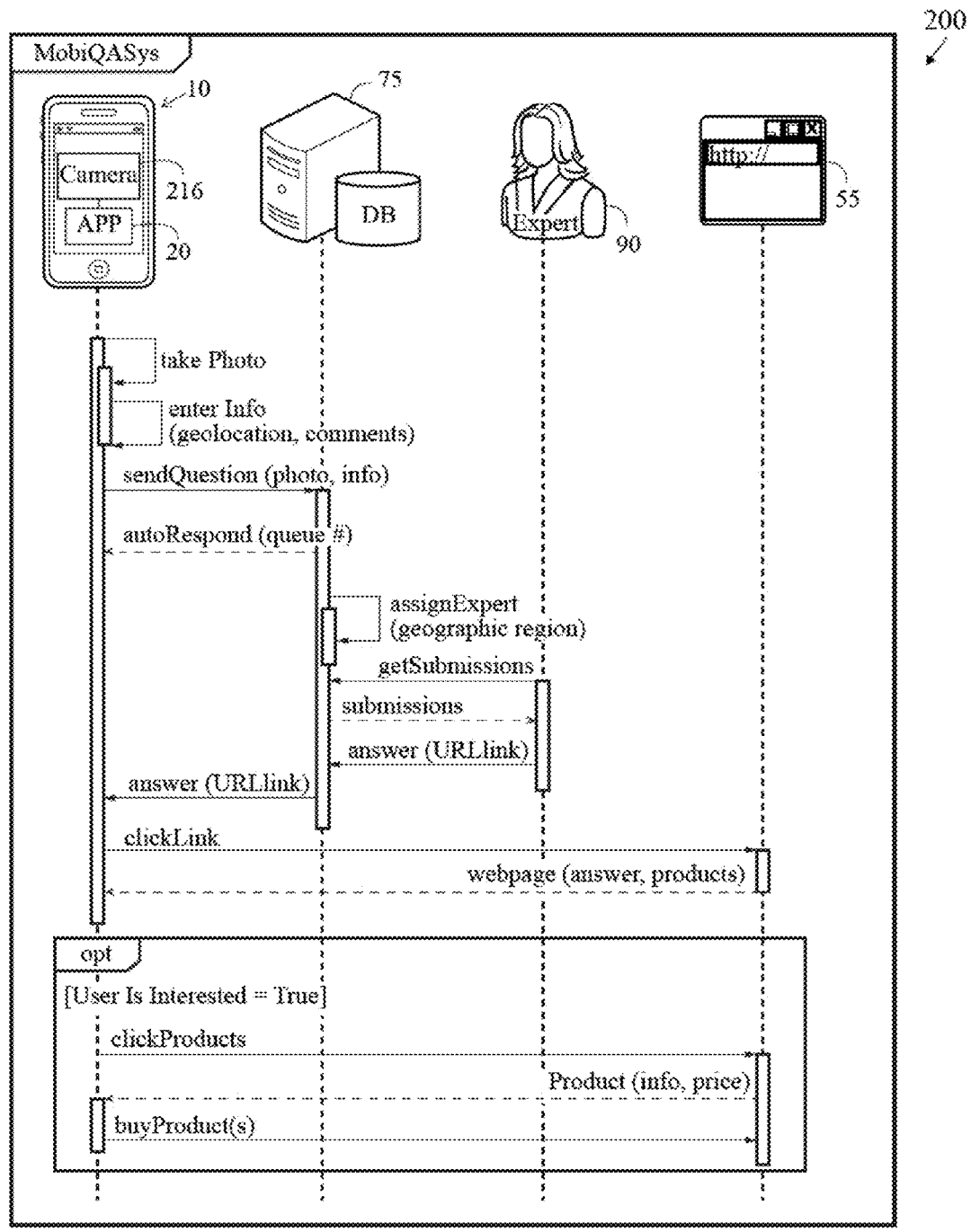
FIG. 20 is a sequence diagram of communication between components within a system of the present invention.

FIG. 20 illustrates a communication sequence diagram for identifying an image of a plant sent from a mobile native application 20 resident on a mobile device 10 to a server 75. An end-user wants to know the name of a plant. The end-user 15 opens the mobile native application 20 and uses a camera component of the mobile device 10 to take an image of the plant. The mobile native application 20 enters geolocation from a GPS component of the device 10 and the end-user enters any additional comments about the plant. The mobile native application 20 sends an image message comprising the image 30, the geolocation and the comments. The image message is sent over a network to a server 75. The sever responds to the image message with a communication that indicates receipt of the image message and a position in a queue for the inquiry. The image message is preferably assigned to an expert 90 on the server-side 75, and the expert prepares an answer based on submissions. Alternatively, the image and data (geolocation and additional comments) from the image message are inputted into an identification algorithm at the server 75 and a response is generated. The server 75 may use recognition software to identify candidates for the submitted plant or disease, and further analysis (for example based on location) reduces the possible candidates to an identified plant or disease.

The answer/response message is sent to the mobile native application 20 on the mobile device 10 of the end user 15. The answer message contains a link. The end user clicks on the link and a webpage is generated on a website for the end user. Additional product information that may be helpful to the end user is provided on the webpage.

The mobile communication devices 10 utilized with the present invention preferably include mobile phones, smartphones, tablet computers, PDAs and the like. Examples of smartphones and the device vendors include the IPHONE® smartphone from Apple, Inc., the DROID® smartphone from Motorola Mobility Inc., GALAXY S® smartphones from Samsung Electronics Co., Ltd., and many more. Examples of tablet computing devices include the IPAD® tablet from Apple Inc., and the XOOM™ tablet from Motorola Mobility Inc.

A mobile communication service provider (aka phone carrier) of the customer such as VERIZON, AT&T, SPRINT, T-MOBILE, and the like mobile communication service providers, provide the communication network for communication to the mobile communication device of the end user.

Wireless standards include 802.11a, 802.11b, 802.11g, AX.25, 3G, CDPD, CDMA, GSM, GPRS, radio, microwave, laser, Bluetooth, 802.15, 802.16, and IrDA.

Figure 21:
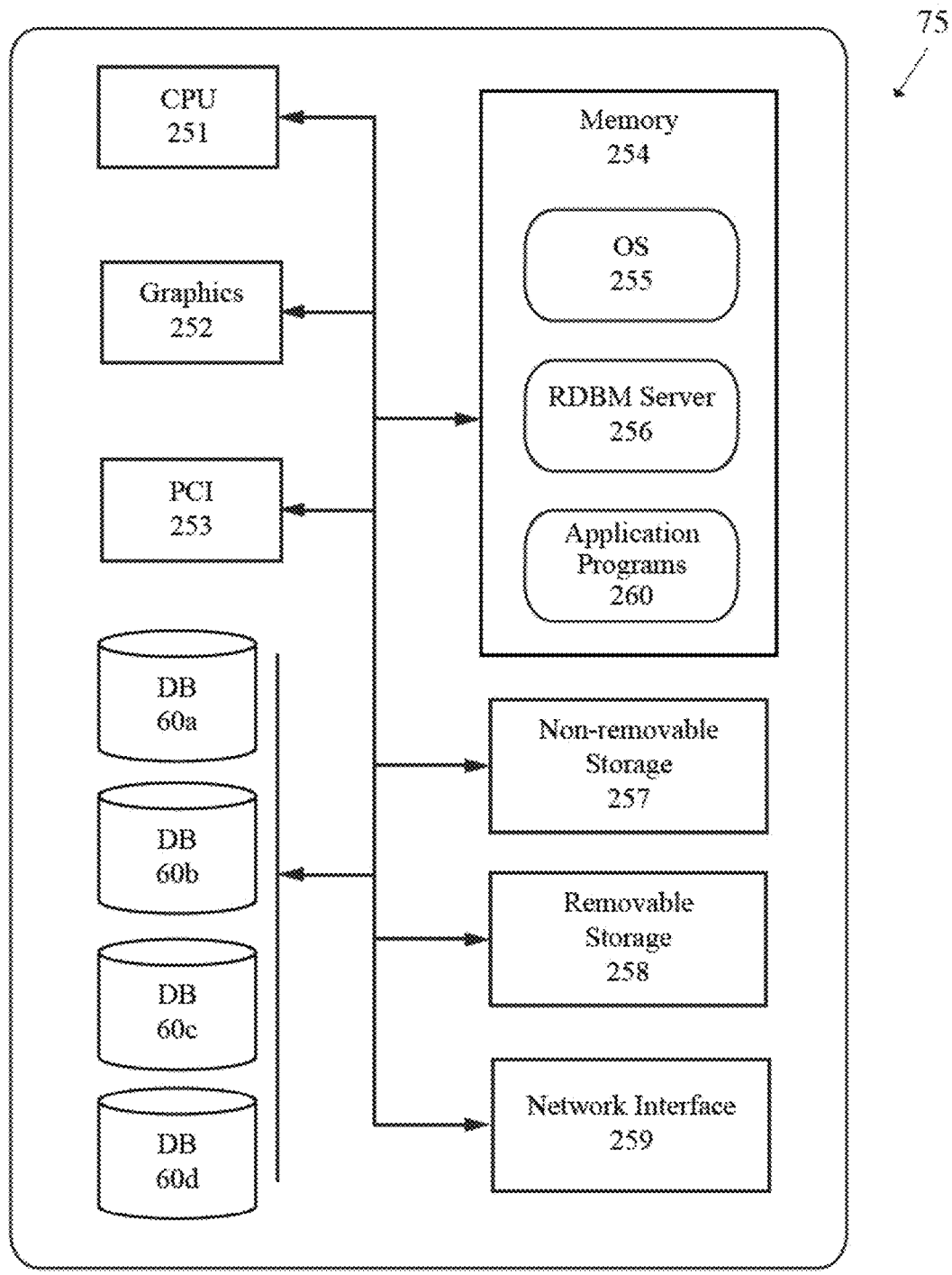
FIG. 21 is a block diagram of components of a server-side computer.

FIG. 21 shows components of a general data server 75 of a system for using a mobile application resident on a mobile communication device to identify an unknown plant or a plant disease. The data server 40 includes a CPU component 301, a graphics component 302, PCI/PCI Express 303, RAM memory 304, non-removable storage 307, removable storage 308, Network Interface 309, including one or more connections to a fixed network 35, and a SQL database 45a-45d. Included in the memory 304 are the operating system 305, the SQL server 306, and computer programs 310. The data server 40 also includes at least one computer program configured to receive data uploads and store the data uploads in the SQL database. The SQL server 306 comprises of other components of SQL server that can be installed separately from the SQL database engine.

Each of the interface descriptions preferably discloses use of at least one communication protocol to establish handshaking or bi-directional communications. These protocols preferably include but are not limited to XML, HTTP, TCP/IP, Serial, UDP, FTP, Web Services, WAP, SMTP, SMPP, DTS, Stored Procedures, Import/Export, Global Positioning Triangulation, IM, SMS, MMS, GPRS and Flash. The databases used with the system preferably include but are not limited to MSSQL, Access, MySQL, Progress, Oracle, DB2, Open Source DBs and others. Operating system used with the system preferably include Microsoft 2010, XP, Vista, 200o Server, 2003 Server, 2008 Server, Windows Mobile, Linux, Android, Unix, I series, AS 400 and Apple OS.

The underlying protocol at a server is preferably Internet Protocol Suite (Transfer Control Protocol/Internet Protocol ("TCP/IP")), and the transmission protocol to receive a file is preferably a file transfer protocol ("FTP"), Hypertext Transfer Protocol ("HTTP"), Secure Hypertext Transfer Protocol ("HTTPS") or other similar protocols. The transmission protocol ranges from SIP to MGCP to FTP and beyond. The protocol at the server is preferably HTTPS.

Figure 19:
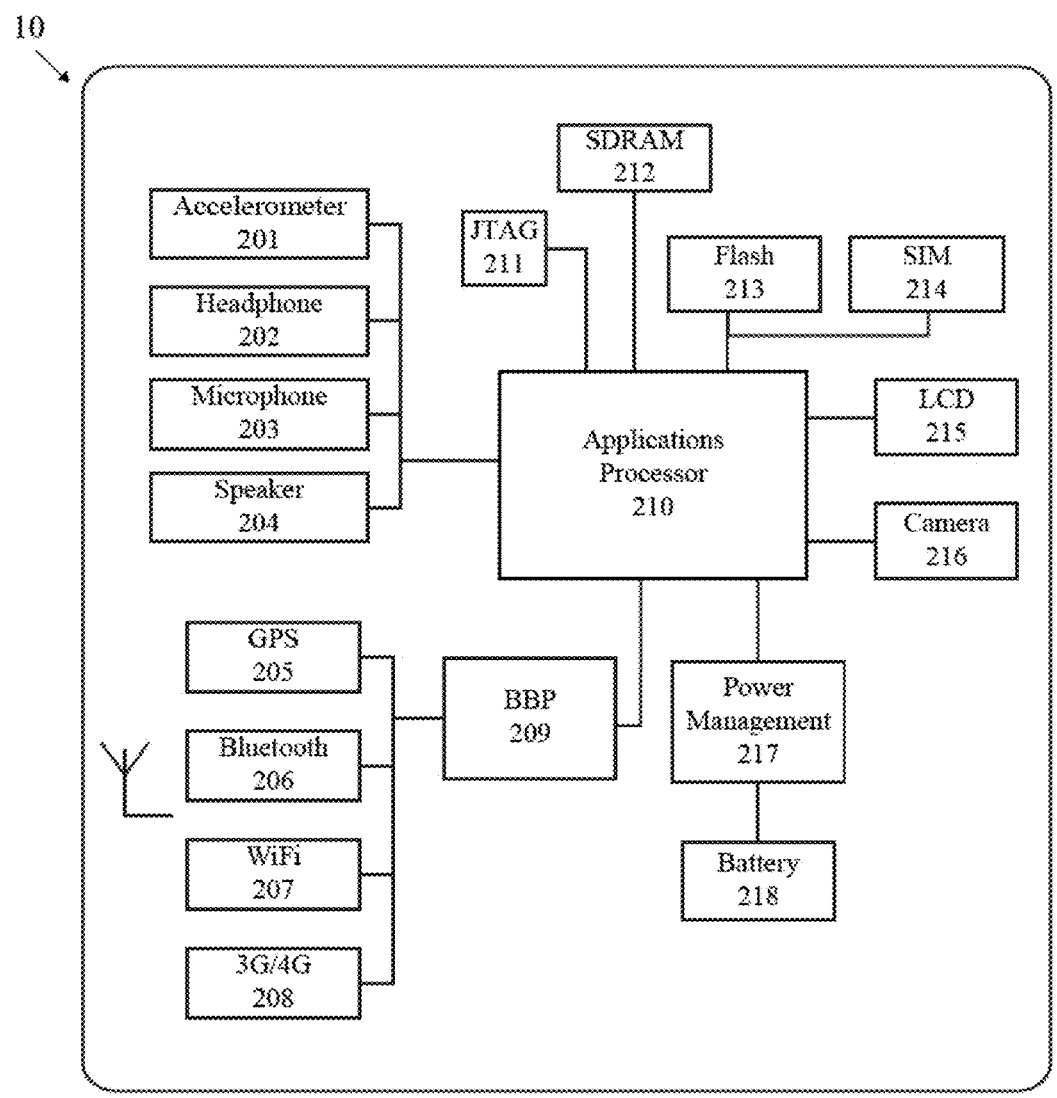
FIG. 19 is a block diagram of components of a mobile communication device.

As shown in FIG. 19, a typical mobile communication device 10 includes an accelerometer 201, a headphone jack 202, a microphone jack 203, a speaker 204, a GPS component 205, a Bluetooth component 206, a Wi-Fi component 207, a 3G/4G component 208, a Baseband Processor (for radio control) 209, an applications processor 210, a JTAG (debugger) 211, a SDRAM memory 212, a Flash memory 213, SIM card 214, LCD display 215, a camera component 216, a power management circuit 217 and a battery or power source 218.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

I claim as my invention the following:

1. A method for using a mobile native application resident on a mobile communication device to identify an unknown plant, the method comprising:

opening a mobile native application on a mobile communication device and accessing a plant identifier page of the mobile native application, wherein the mobile native application is downloaded from an APP STORE over a network to the mobile communication device, and the mobile native application is resident in a memory of the mobile communication device, and the mobile native application is configured for the operating system of the mobile communication device;

taking an image of a plant unknown to an end-user of the mobile communication device;

transmitting the image of the plant as an image inquiry message over a network to a server;

receiving the image inquiry message at the server from the mobile native application of the mobile communication device over the network, the mobile communication device comprising a camera component and a GPS component, the image inquiry message comprising the image, geographical location information for the image, and an optional plurality of comments about the image, optionally categorizing the image into a predetermined category selected from the group consisting of flower, tree, vegetable, fruit, house plant, weed, lawn, pest and plant disease, provided by an end user, wherein the image is of a plant, plant disease or plant pest, wherein the image inquiry message concerns the identification of the plant, plant disease or plant pest;

analyzing the image at the server to determine if the image is acceptable;

transferring the image at the server for substantive content analysis;

analyzing the image to generate a color and texture feature vector for the plant;

comparing the color and texture feature vector to a database of available plants;

utilizing recognition software to identify candidates for the plant, plant disease or plant pest;

preparing a response at the server to identify the plant, plant disease or plant pest, wherein the response is based on the image, the geographical location, the comments, and information contained in the database of the server; and transmitting a response message from the server to the mobile native application of the mobile communication device, wherein the response message identifies a plurality of possible plant, plant disease or plant pest matches, and provides product information for the identified plant, plant disease or plant pest;

wherein if the end-user cannot visually determine a match from the plurality of possible matches, the end-user then requests the opinion of an human expert from the mobile communication device;

wherein the request is passed from the mobile communication device to the server;

wherein the original identification request and the server-generated response message are sent to the expert;

wherein the expert is provided a web site to view the end-user request, and the server generated response;

wherein the expert uses the web site to filter identification candidates by common name, Latin name, category, user comments, color, texture, or geolocation;

wherein the expert generates a second response message identifying the plant or disease from an existing database entry, by modifying an existing database entry, or by creating a new response which is stored in the database;

wherein the second response is sent from the server to the mobile communication device.

* * * * *